US008362144B2

(12) United States Patent
Martin et al.

(10) Patent No.: US 8,362,144 B2
(45) Date of Patent: Jan. 29, 2013

(54) MONOMERS FOR MAKING POLYMERIC CELL CULTURE SURFACE

(75) Inventors: Arthur W. Martin, Horseheads, NY (US); Shawn M. O'Malley, Horseheads, NY (US); Simon K. Shannon, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 413 days.

(21) Appl. No.: 12/783,156

(22) Filed: May 19, 2010

(65) Prior Publication Data

US 2011/0152455 A1 Jun. 23, 2011

Related U.S. Application Data

(60) Provisional application No. 61/180,287, filed on May 21, 2009.

(51) Int. Cl.
*C08F 222/40* (2006.01)
*C08F 22/40* (2006.01)
*C08F 20/00* (2006.01)
*C07D 207/46* (2006.01)

(52) U.S. Cl. .......... 525/54.1; 526/262; 526/303.1; 548/542

(58) Field of Classification Search .......... 525/54.1; 526/262, 303.1; 548/542
See application file for complete search history.

(56) References Cited

U.S. PATENT DOCUMENTS

| | | | |
|---|---|---|---|
| 3,502,545 A | 3/1970 | Westman et al. | 195/66 |
| 4,578,079 A | 3/1986 | Ruoslahti et al. | 523/11 |
| 4,792,525 A | 12/1988 | Ruoslahti et al. | 435/240.243 |
| 4,908,236 A | 3/1990 | Pitt et al. | 427/245 |
| 5,278,063 A | 1/1994 | Hubbell et al. | 435/240.243 |
| 5,330,911 A | 7/1994 | Hubbell et al. | 435/240.243 |
| 5,480,953 A | 1/1996 | Sugaya et al. | 526/320 |
| 5,643,561 A | 7/1997 | Katsuen et al. | 424/78.17 |
| 5,691,203 A | 11/1997 | Katsuen et al. | 435/402 |
| 5,695,997 A | 12/1997 | Ruoslahti et al. | 435/375 |
| 5,916,875 A | 6/1999 | Ruoslahti et al. | 514/12 |
| 6,121,027 A | 9/2000 | Clapper et al. | 435/180 |
| 6,306,922 B1 | 10/2001 | Hubbell et al. | 522/71 |
| 6,316,522 B1 | 11/2001 | Loomis et al. | 523/105 |
| 6,514,734 B1 | 2/2003 | Clapper et al. | 435/180 |
| 7,067,194 B2 * | 6/2006 | Mao et al. | 428/429 |
| 7,384,984 B2 | 6/2008 | Lewandowski et al. | 514/772.1 |
| 7,402,339 B2 | 7/2008 | Schmidt et al. | 428/407 |
| 2003/0083389 A1 | 5/2003 | Kao et al. | 516/98 |
| 2003/0215946 A1 | 11/2003 | Nair et al. | 435/395 |
| 2005/0019747 A1 | 1/2005 | Anderson et al. | 435/4 |

(Continued)

FOREIGN PATENT DOCUMENTS

| | | |
|---|---|---|
| EP | 0614923 B1 | 1/2000 |
| JP | 2002-191353 | 7/2002 |

(Continued)

OTHER PUBLICATIONS

Anderson, Daniel G., Levenberg, Shulamit, Langer, Robert, Nanoliter-scale synthesis of arrayed biomaterials and application to human embryonic stem cells, Nature Biotechnology vol. 22, No. 7, Jul. 2004, 863-866.

(Continued)

*Primary Examiner* — William Cheung
(74) *Attorney, Agent, or Firm* — Susan S. Wilks

(57) ABSTRACT

N-hydroxysuccinimide acrylate ester monomers are described which provide N-hydroxysuccinimide derivatized monomers for the formation of polymeric cell culture surfaces suitable for culture of difficult to culture cells including undifferentiated embryonic stem cells. Methods of making the monomers and are also described.

6 Claims, 5 Drawing Sheets

U.S. PATENT DOCUMENTS

| | | |
|---|---|---|
| 2005/0036980 A1 | 2/2005 | Chaney et al. ............ 424/78.27 |
| 2005/0136536 A1 | 6/2005 | Anderson et al. ............ 435/366 |
| 2005/0276858 A1 | 12/2005 | Kao et al. .................... 424/487 |
| 2005/0281857 A1 | 12/2005 | Heyer et al. .................. 424/423 |
| 2006/0100369 A1 | 5/2006 | Kao et al. .................... 525/54.1 |
| 2006/0127878 A1 | 6/2006 | Salomon et al. ................. 435/4 |
| 2006/0134050 A1 | 6/2006 | Griffith et al. ............ 424/70.16 |
| 2006/0263878 A1 | 11/2006 | Mochitate .................... 435/366 |
| 2007/0026518 A1 | 2/2007 | Healy et al. .................. 435/325 |
| 2007/0167354 A1 | 7/2007 | Kennedy et al. .................. 514/8 |
| 2009/0043079 A1 | 2/2009 | Chen et al. .................... 530/402 |

FOREIGN PATENT DOCUMENTS

| | | |
|---|---|---|
| JP | 2006-174826 | 7/2006 |
| WO | 02/062969 A2 | 8/2002 |
| WO | 03/029418 A2 | 4/2003 |
| WO | 2004/037164 A2 | 5/2004 |
| WO | 2006/105278 A2 | 10/2006 |
| WO | 2007/104107 A1 | 9/2007 |

OTHER PUBLICATIONS

Barber, T.A., Harbers, G.M., Park, S., Gilbert, M., Healy, K.E., "Ligand Density Characterization of Peptide-Modified Biomaterials," Biomaterials, 26(34), 6897-6905 (2005).

Barber, T.A., Golledge, S.L., Castner, D.G, and Healy, K.E., "Peptide-modified p(AAm-co-EG/AAc) IPNS Grafted to Bulk Titanium Modulate Osteoblast Behavior In Vitro," J. Biomed. Mater. Res., 64A, 38-47 (2003).

Bearinger, J.P., Castner, D.G., and Healy, K.E., "Biomolecular Modification of P(AAm-co-EG/AA) IPNs Supports Osteoblast Adhesion and Phenotypic Expression," J. Biomaterials Science:Polymer Ed., 9(7), 629-652 (1998).

Bearinger, J.P., Castner, D.G., Chen, J., Hubchak, S., Golledge, S.L., and Healy, K.E., "P(AAm-co-EG) Interpenetrating Polymer Networks Grafted to Oxide Surfaces: Surface Characterization, Protein Adsorption, and Cell Detachment Studies," Langmuir, 13(19), 5175-5183 (1997).

Braam, Stefan R., et al., Recombinant Vitronectin Is a Functionally Defined Substrate that Supports Human Embryonic Stem Cell Self Renewal Via AVB5 Integrin, Stem Cells express, Jul. 3, 2008, 1-20.

Drumheller PD, Herbert CB, Hubbell JA; "Bioactive Peptides and Surface Design", Interfacial Phenomena and Bioproducts, J.L. Brash et al., Marcel Dekker, Inc, 1996, pp. 273-310.

Cruise GM, Scharp DS, and Hubbell JA. Characterization of permeability and network structure of interfacially photopolymerized poly(ethylene glycol) diacrylate hydrogels. Biomaterials 19: 1287-1294, 1998.

Dawson, Eileen, et al., "Biomaterials for stem cell differentiation", Advanced Drug Delivery Reviews, vol. 60, 2008, 215-228.

Drumheller, Paul D., Elbert, Donald L., Hubbell, Jeffrey A., Multifunctional Poly(ethylene glycol) Semi-Interpenetrating Polymer Networks as Highly Selective Adhesive Substrates for Bioadhesive Peptide Grafting, Biotechnology and Bioengineering, vol. 43, pp. 772-780, (1994).

Drumheller PD and Hubbell JA. Polymer networks with grafted cell adhesion peptides for highly biospecific cell adhesive substrates. Anal Biochem 222: 380-388, 1994.

Drumheller P.D. and Hubbell J.A.: Surface immobilization of adhesion ligands for investigations of cell/substrate interactions. In: The Biomedical Engineering Handbook, J.D. Bronzino Ed., CRC and IEEE Press 1583-1596, 1995.

Harbers G.M., Healy, K.E., "The Effect of Ligand Type and Density on Osteoblast Adhesion, Proliferation, and Matrix Mineralization," J. Biomed. Mater. Res. Part A, 75A, 855-869 (2005).

Healy, K.E., Rezania, A., and Stile, A., "Designing Biomaterials to Direct Biological Responses," Annals of the New York Academy of Sciences, 875, 24-35 (1999).

Healy, K.E., "Molecular Engineering of Materials for Bioreactivity," Current Opinion in Solid State and Materials Science, 4, 381-387 (1999).

Heggli M, Tirelli N, Zisch A, and Hubbell JA. Michael-type addition as a tool for surface functionalization. Bioconjug Chem 14: 967-973, 2003.

Hern DL and Hubbell JA. Incorporation of adhesion peptides into nonadhesive hydrogels useful for tissue resurfacing. J Biomed Mater Res 39: 266-276, 1998.

Hubbell JA. Biomaterials in tissue engineering. Biotechnology (NY) 13: 565-576, 1995.

Hubbell JA, Massia SP, and Drumheller PD. Surface-grafted cell-binding peptides in tissue engineering of the vascular graft. Ann N Y Acad Sci 665: 253-258, 1992.

Huebsch, N., Gilbert, M., Healy, K.E., "Analysis of Sterilization Protocols for Peptide-Modified Hydrogels," J. Biomed. Mater. Res. Part B, 74B(1), 440-447 (2005).

Irwin, E.F., Ho, J.E., Kane, S.R., Healy, K.E, "Analysis of Interpenetrating Polymer Networks via Quartz Crystal Microbalance with Dissipation Monitoring," Langmuir, 21(12), 5529-5536 (2005).

Kim, S.-Y., Chung, E., Gilbert, M., and Healy, K.E., "Synthetic MMP-13 Degradable ECMs Based on Poly(N-isopropyl acrylamide-co-Acrylic acid) Semi-Interpenetrating Polymer Networks I. Degradation and Cell Migration," J. Biomed. Mater. Res. Part A, 75(1), 73-88 (2005).

Kim, S.-Y., and Healy, K.E, "Synthesis and Characterization of Injectable Poly(N-isopropyluerylamide-co-Acrylic acid) Hydrogels with Proteolytically Degradable Cross-links," Biomacromolecules, 4, 1214-1223 (2003).

Li Y, Powell S, Brunette E, Lebkowski J, Mandalam R. Expansion of human embryonic stem cells in defined serum-free medium devoid of animal-derived products. Biotechnol Bioeng. 91(6):688-98, 2005.

Li, Y.J., Chung, E.H., Rodriguez, R.T., Firpo, M.T., Healy, K.E., "Hydrogels as Artificial Matrices for Human Embryonic Stem Cell Self-Renewal," J. Biomed. Mater. Res. Part A, 79(1), 1-5 (2006).

Lu J. Hou R, Booth C, Yang S, Snyder M. Defined culture conditions of human embryonic stem cells. PNAS USA. 103(15):5688-93, 2006.

Lutolf MP and Hubbell JA. Synthetic biomaterials as instructive extracellular microenvironments for morphogenesis in tissue engineering. Nat Biotechnol 23: 47-55, 2005.

Lutolf MP and Hubbell JA. Synthesis and physicochemical characterization of end-linked poly(ethylene glycol)-co-peptide hydrogels formed by Michael-type addition. Biomacromolecules 4: 713-722, 2003.

Massia SP and Hubbell JA. An RGD spacing of 440 nm is sufficient for integrin alpha V beta 3-mediated fibroblast spreading and 140 nm for focal contact and stress fiber formation. J Cell Biol 114: 1089-1100, 1991.

Massia SP, Rao SS, and Hubbell JA. Covalently immobilized laminin peptide Tyr-Ile-Gly-Ser-Arg (YIGSR) supports cell spreading and co-localization of the 67-kilodalton laminin receptor with alpha-actinin and vinculin. J Biol Chem 268: 8053-8059, 1993.

Massia SP and Hubbell JA. Human endothelial cell interactions with surface-coupled adhesion peptides on a nonadhesive glass substrate and two polymeric biomaterials. J Biomed Mater Res 25: 223-242, 1991.

Massia SP and Hubbell JA. Immobilized amines and basic amino acids as mimetic heparin-binding domains for cell surface proteoglycan-mediated adhesion. J Biol Chem 267: 10133-10141, 1992.

Massia SP and Hubbell JA. Vascular endothelial cell adhesion and spreading promoted by the peptide REDV of the IIICS region of plasma fibronectin is mediated by integrin alpha 4 beta I. J Biol Chem 267: 14019-14026, 1992.

Model, M., and Healy, K.E., "Quantification of the Surface Density of a Fluorescent Label with the Optical Microscope," J. Biomed. Mater. Res., 50, 90-96 (2000).

Park, S., Bearinger, J.P., Lautenschlager, E.P., Cashier, D.G., Healy, K.E., "Surface Modification of Poly(ethylene terephthalate) Angioplasty Balloons with a Hydrophilic Poly(acrylamide-co-ethylene glycol) Interpenetrating Network Coating," J. Biomed. Mater. Res., 53(5), 568-576 (2000).

Pratt, A.B., et al., Synthetic Extracellular Matrices for In Situ Tissue Engineering, Biotechnology and Bioengineering, vol. 86, No. 1, Apr. 5, 2004, 27-36.

Saha et al., Journal of Biomedical Materials Research Part A, Biomimetic interfacial interpenetrating polymer networks control neural stem cell behavior, (2007), 81(1):240-249.

Stile, R. A., Shull, K.R., and Healy, K. E., "Axisymmetric Adhesion Test to Examine the Interfacial Interactions between Biologically-Modified Networks and Models of the Extracellular Matrix," Langmuir, 19, 1853-1860 (2003).

Stile R.A., Chung E., Burghardt, W.R., Healy, K.E., "Poly(N-isopropylacrylamide)-based Semi-Interpenetrating Polymer Networks for Tissue Engineering Applications. Effects of Linear Poly(acrylic acid) Chains on Rheology," J. Biomater. Sci. Polym. Ed., 15(7), 865-878 (2004).

Stile, R.A., and Healy, K.E., "Poly(N-isopropylacrylamide)-based Semi-Interpenetrating Polymer Networks for Tissue Engineering Applications Effects of Linear Poly(acrylic acid) Chains on Phase Behavior," Biomacromolecules, 3, 591-600 (2002).

Thomas, C.H., L'Hoest, J-B., Castner, D.G., McFarland, C.D., and Healy, K.E., "Materials Designed to Control and Examine the Function of Single Cells," Mat. Res. Soc. Symp. Proc., 530, 55-58 (1998).

* cited by examiner

MONOMERS FOR MAKING POLYMERIC CELL CULTURE SURFACE

CLAIMING BENEFIT OF PRIOR FILED U.S. APPLICATION

This application claims the benefit of U.S. Provisional Application Ser. No. 61/180,287 entitled "Monomers for Making Polymeric Cell Culture Surface" filed on May 21, 2009 the contents of which are hereby incorporated by reference herein.

FIELD

The present invention relates generally to monomers for making surfaces to support cell culture, and methods of making the monomers. More specifically, the present invention relates to N-hydroxysuccinimide derivatized (meth)acrylate monomers used, in combination with other (meth)acrylate compounds to form polymeric cell culture surfaces. The present invention also provides methods for making the derivatized monomers.

SEQUENCE LISTING

This application contains a Sequence Listing electronically submitted via EFS-Web to the United States Patent and Trademark Office as text filed named "SEQUENCE_LISTING_SP09-150_ST25.txt" having a size of 6 kb and created on Feb. 23, 2011. Due to the electronic filing of the Sequence Listing, the electronically submitted Sequence Listing serves as both the paper copy required by 37 CFR §1.821(c) and the CRF required by §1.821(e). The information contained in the Sequence Listing is hereby incorporated herein by reference.

BACKGROUND

In vitro culturing of cells has been a useful research tool, providing material necessary for research in pharmacology, physiology and toxicology. Recent advances in the field of developmental biology, significantly in the isolation, growth and differentiation of stem cells, have opened the door for cell culture to provide material for therapeutic applications as well. Embryonic stem cells, including human embryonic stem cells, may be able to provide answers to difficult medical problems such as Alzheimer's disease, Parkinson's disease, diabetes, spinal cord injury, heart disease, and other debilitating and often fatal conditions.

Embryonic stem cells represent an example of difficult-to-culture cell types. Embryonic stem cells are particularly difficult to culture, difficult to control, and often require a specialized cell culture surface that can facilitate growth and proliferation of these cells in their undifferentiated state. Many coatings and surface enhancements have been developed to provide cell culture surfaces which promote cell growth in vitro. Some of these coatings and surface enhancements provide surfaces that support the culture of difficult-to-culture cells such as embryonic stem cells. However, many of these surfaces contain animal-derived additives such as proteins or cell extracts. These additives introduce a risk of infection into the preparation of therapeutic cells. For example, the use of extra-cellular matrix proteins derived from animals may introduce infective agents such as viruses or prions. These infective agents may be taken up by cells in culture and, upon the transplantation of these cells into a patient, may be taken up into the patient. Therefore, the addition of these factors in or on cell culture surfaces may introduce new disease even as they address an existing condition. In addition, these animal-derived additives or cell surface coatings may lead to significant manufacturing expense and lot-to-lot variability which are not preferable. There is a need for cell culture surfaces which do not include animal-derived ingredients or additives and which provide cell culture conditions amenable for cell culture, including the culture of difficult-to-culture cells such as embryonic stem cells.

SUMMARY

Embodiments of the present invention provide N-hydroxysuccinimide (meth)acrylate monomers, mono-(2-methacryloyloxyl)-ethyl succinate N-hydroxysuccinimide ester and 2-carboxyethyl acrylate N-hydroxysuccinimide ester. These monomers can be polymerized to form polymers, either alone or in combination with other monomers. In embodiments these monomers are polymerized with a hydrophilic monomer and a cross-linker monomer. In embodiments, the hydrophilic monomer is 2-hydroxyethyl methacrylate and the cross-linker monomer is tetraethyleneglycol dimethacrylate. In embodiments, the present invention provides a synthetic polymeric cell culture surface made from these polymers.

Embodiments provide a peptide-conjugated polymeric cell culture surface having a polymer made from mono-(2-methacryloyloxyl)-ethyl succinate N-hydroxysuccinimide ester, 2-hydroxyethyl methacrylate, and tetraethyleneglycol dimethacrylate wherein the polymer is conjugated to an RGD-containing peptide. Or, in embodiments, the invention provides a peptide-conjugated polymeric cell culture surface comprising a polymer made from 2-carboxyethyl acrylate N-hydroxysuccinimide ester, 2-hydroxyethyl methacrylate, and tetraethyleneglycol dimethacrylate where the polymer is conjugated to an RGD-containing peptide. In embodiments, the peptide-conjugated polymeric cell culture surface wherein contains the peptide KGGNGEPRGDTYRAY (SEQ ID NO:1).

DETAILED DESCRIPTION

Figure 1:
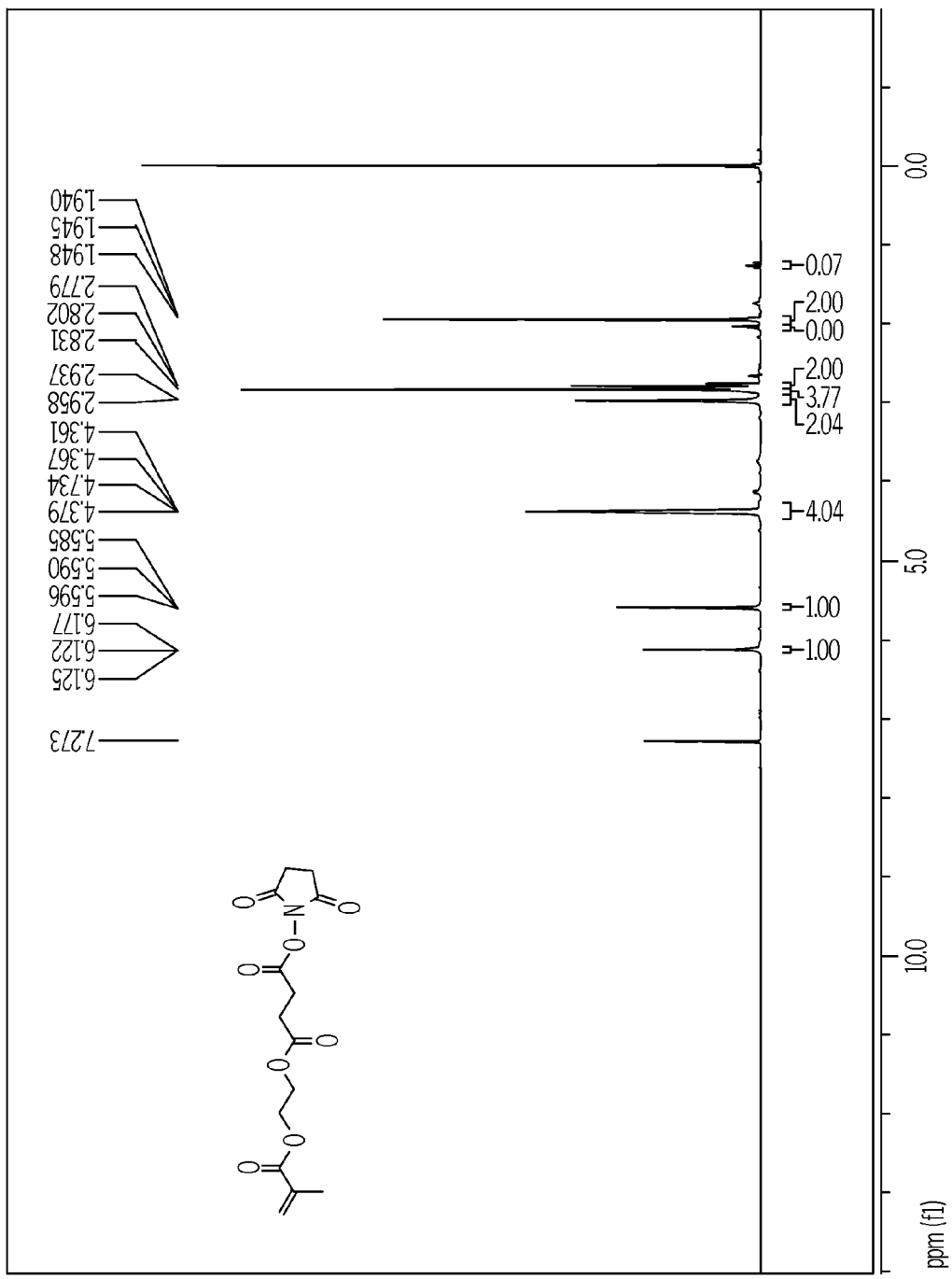
FIG. 1 is an NMR spectra of mono-(2-methacryloyloxyl)-ethyl succinate N-hydroxysuccinimide (MOES-NHS) ester, compound 2.

Embodiments of the present invention provide N-hydroxysuccinimide (NHS) derivatized monomers for use in making polymer surfaces which provide cell culture surfaces suitable for culturing cells including difficult-to-culture cells such as embryonic stem cells. In embodiments, the N-hydroxysuccinimide (NHS)—derivatized monomers can be used to form polymer surfaces with a pendant NHS moiety to conjugate peptides or proteins to the polymer surfaces, including peptides which provide cell adherent sequences such as RGD sequences.

In embodiments, the present invention provides cost effective methods for processing functionalized polymer coatings for cell culture. NHS modification of a carboxyl group prior to polymerization eliminates the need for a NHS surface activation step in an underivatized polymer (reducing the use of excess reagents and solvents for activation and washing of the surface). Thus, these new monomers may enable a cost effective and easily scalable method to reduce the number of processing steps for preparing polymeric cell culture surfaces. In addition, in embodiments, these monomers may increase the conjugation efficiency of peptides to polymeric cell culture surfaces. In additional embodiments, methods for making these NHS-functionalized monomers are provided.

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "monomer" means a compound capable of polymerizing with another monomer, (regardless of whether the "monomer" is of the same or different compound than the other monomer), which compound has a molecular weight of less that about 1000 Dalton. In many cases, monomers will have a molecular weight of less than about 400 Dalton.

As used herein, "hydrophilic monomer" means monomers that form a surface which has a low contact angle. In embodiments of the present invention, synthetic polymer surfaces made from monomers and combinations of monomers which were more hydrophilic provided improved surfaces for cell growth.

As used herein, "conjugator monomer" means an NHS-functionalized (meth)acrylate monomer which can be used to conjugate a peptide (polypeptide, protein or other bioactive compound) to a surface. In embodiments the surface is a synthetic polymer surface.

As used herein, "cross-linker monomer" means monomers which have more than one polymerization moiety which can form a bond with another monomer to form a cross-link. In embodiments, the polymerization moiety may be (meth)acrylate moieties. The higher the percentage of cross-linking monomers in a mixture, the more cross-linked the cell culture surface will be. More cross-linked surfaces are harder surfaces. These hard surfaces are less likely to absorb water. If they are charged monomers, they may provide good wetability, and therefore high measured modulus while at the same time, these surfaces may be hard, non-porous surfaces. Highly crosslinked surfaces are not hydrogels. That is, they do not absorb liquid. These surfaces because of their physical properties outlined may also adsorb small and large biomolecules present in the cell culture media and or proteins produced during cell growth which may further enhance growth and proliferation of cells including stem cells on the surface. In addition, cross-linker monomers can be hydrophilic. For example glycerol-1,3-diglycerolate diacrylate and 3-(Acryloyloxy)-2-hydroxypropyl methacrylate are hydrophilic crosslinkers. For example, glycerol monomethacrylate is more hydrophilic than HEMA.

As used herein, "cyclic olefin copolymer" means a polymer formed from more than one monomer species, where at least one of the monomer species is a cyclic olefin monomer and at least one other monomer species is not a cyclic olefin monomer species. In many embodiments, cyclic olefin copolymers are formed from ethylene and norbonene monomers. Cyclic olefin copolymer resins are commercially available with trade name of TOPAS® from Boedeker Plastics, Inc.

Unless stated otherwise, ratios of compounds in a composition, such as a solution, are stated on a by volume basis.

As used herein, "have", "having", "include", "including", "comprise", "comprising" or the like are used in their open ended sense, and generally mean "including, but not limited to".

The present disclosure describes, inter glia, articles for culturing cells, methods for producing articles for cell culture and methods for screening surfaces for their ability to support cultured cells. Various embodiments presented herein provide for the ability to produce uniform, non-toxic synthetic polymer coatings for use in high throughput screening to identify synthetic coatings that provide favorable interactions with cultured cells.

(Meth)acrylate monomers and combinations of (meth) acrylate monomers have been shown to support embryonic stem cells in culture (see application Ser. Nos. 12/362,782 and 12/362,924, both filed 30 Jan. 2009, and incorporated herein by reference in their entirety to the extent that it does not conflict with the present disclosure). Embryonic stem cells (ESCs), including human embryonic stem cells (hESCs), are able to grow and self-renew unlimitedly; they can be propagated in culture for extended periods and have an ability to differentiate to multiple cell types. However, these cells have specific cell culture needs. Slight changes in culture conditions can cause these cells to differentiate, or exhibit reduced growth and propagation characteristics. In many cases, ESC cultures require the addition of animal-derived materials either in or on a cell culture surface to effectively grow in culture. These animal-derived materials may harbor pathogens such as infective proteins and viruses, including retroviruses. Although some substrates have demonstrated the ability to facilitate proliferation of ESC in both un-differentiated (pluripotent) and differentiated states, they may still be considered inadequate for cell cultures that are directed toward the development of cell therapeutics in humans because of the threat of pathogens that might be carried from an animal source of cell culture additives to the cultured cells, to an individual treated with those cells. In addition, these animal-derived surfaces may have high lot-to-lot variability making results less reproducible, and they may be very expensive. In light of these disadvantages, surfaces that include animal-derived materials may be relegated to academic and pre-clinical research and may not be useful to produce, for example, stem cells to treat patients. Furthermore, because of the costs associated with these animal derived surfaces, they are considered very expensive even for academic research, leaving the door open for cheaper and safer alternatives. Therefore, to provide a product which eliminates the risks associated with animal derived products, synthetic (meth)acrylate surfaces with special surface attributes, and improved methods of making these surfaces are proposed.

In embodiments, cell culture surfaces may be made from ingredients which are not animal-derived, may sustain at least 15 passages of cells in cell culture, may be reliable and reproducible, and may allow for the growth of cells which show normal characteristics, normal karyotype, after defined passages. Cell culture surfaces for stem cells may be made from ingredients which are not animal-derived, and sustain undifferentiated growth of ES cells for at least 10 passages in culture. In embodiments, cell culture surfaces may also be stable. Cell culture surfaces may be non-toxic. They may be able to withstand processing conditions including sterilization, possess adequate shelf life, and maintain quality and function after normal treatment. In addition, preferable cell culture surfaces may be suitable for large-scale industrial production. They may be scalable and cost effective to produce. The materials may also possess chemical compatibility with aqueous solutions and physiological conditions found in cell culture environments.

Cell culture studies conducted on synthetic surfaces have demonstrated that surface properties of substrates can affect the success of cell culture and can affect characteristics of cells grown in culture. For example, surface properties can elicit cell adhesion, spreading, growth and differentiation of cells. Research conducted with human fibroblast cells 3T3 and HT-1080 fibrosarcoma cells has shown correlation with surface energetics, contact angle, surface charge and modulus (Altankov, G., Richau, K., Groth, T., The role of surface zeta potential and substratum chemistry for regulation of dermal fibroblasts interaction, Mat.-wiss. U. Werkstofflech. 2003, 34, 12, 1120-1128.) Anderson et al (2005/0019747) disclosed depositing microspots of (meth)acrylates, including polyethylene glycol (meth)acrylates, onto a substrate as surfaces for stem cell-based assays and analysis. Self-Assembled Monolayers (SAMS) surfaces with covalently linked laminin adhesive peptides have been used to enable adhesion and short-term growth of undifferentiated hES cells (Derda, S., Li, Lingyin, Orner, B. P., Lewis, R. L., Thomson, A. J., Kiessling, L. L., Defined Substrates for Human Embryonic Stem Cell Growth Identified from surface Arrays, ACS Chemical Biology, Vol. 2, No. 5, May 2, 2007, pp 347-355.

In embodiments of the present invention, polymeric surfaces composed of cross-linked blends of (meth)acrylate monomers that impart specific physical and chemical attributes to the surface, and methods of making these surfaces are provided. These specific physical and chemical attributes may facilitate the proliferation difficult-to-culture cells such as undifferentiated hESCs in embodiments of the present invention. These (meth)acrylate surfaces are made from monomers with different properties. The monomers have particular characteristics which, when combined and polymerized or cross-linked, provide (meth)acrylate surfaces that are amenable for cell culture. These characteristics may include hydrophilicity or hydrophobicity, positive charge, negative charge or no charge, and compliant or rigid surfaces. For example, monomers or combinations of monomers which are hydrophilic may provide cell culture surfaces that are preferable in embodiments of the present invention. Or, monomers or combinations of monomers which carry a charge may be preferable in embodiments of the present invention. Or, monomers or combinations of monomers which fall within a certain range of modulus or hardness may be preferable in embodiments of the present invention. Or, monomers or combinations of monomers which exhibit a combination of these attributes may be preferable in embodiments of the present invention.

Surfaces for cell culture can be described according to their characteristics such as hydrophobicity, hydrophilicity, surface charge or surface energy, wettability or contact angle, topography, modulus which describes the surface's stiffness versus compliance, degree of cross-linking of polymers, as well as chemical characteristics such as the surface expression of active chemical moieties such as oxygen or nitrogen.

In embodiments, methods of making these surfaces may provide improvements in the cost and expense of manufacturing polymeric or synthetic cell culture surfaces. For example, improved methods may require fewer steps or take less time, require fewer raw materials, require less toxic ingredients or create less toxic by-products, or provide better surfaces, than previously disclosed methods.

In embodiments, reactive N-hydroxysuccinimide (NHS) acrylate monomers (conjugator monomers) for the preparation of peptide-conjugated synthetic polymer surfaces are provided. Instead of forming polymers from mixtures of monomers including carboxyl functionalized (meth)acrylate monomers which are later activated by NHS before peptide conjugation, in embodiments of the present invention, mixtures of (meth)acrylate monomers including reactive N-hydroxysuccinimide (NHS) acrylate monomers are polymerized to form synthetic polymeric cell culture surfaces. NHS modification of the carboxyl-containing monomer prior to polymerization eliminates the need for the NHS surface activation step (reducing the use of excess reagents and solvents for activation and washing of the surface). Thus, embodiments of the monomers disclosed here may enable a cost effective and easily scalable method and reduce the number of processing steps for preparing the synthetic polymeric cell culture surfaces. In addition, these new conjugator monomers may increase the peptide conjugation efficiency of the present formulation and derivatives thereof.

In embodiments of the present invention, methods of synthesizing novel reactive NHS (meth)acrylate monomers are provided. In an embodiment, a reactive NHS acrylate monomer was synthesized by the 1-(3-dimethylaminopropyl)-3-ethyl-carbodiimide hydrochloride (EDC)-mediated esterification of mono-(2-methacryoyloxyl)-ethyl succinate (compound 1), with NHS (in DMF), yielding the corresponding NHS ester, mono-(2-methacryloyloxyl)-ethyl succinate N-hydroxysuccinimide ester (MOES-NHS) (compound 2) in moderate yields and >95% purity. The resulting (compound 2) was a compound having the chemical formula: $C_{14}H_{17}NO_8$ and a molecular weight of 327.29. This was confirmed by $^1H$ NMR shown in FIG. 1. Compound 2 is named, according to IUPAC conventions, 2,5-dioxopyrrolidin-1-yl 1-{2-[(2-methylprop-2-enoyl)oxy]ethyl}butanedioate, and may also be referred to as: 2,5-dioxopyrrolidin-1-yl 2-(methacryloyloxy) ethyl succinate. For the purposes of this disclosure, this compound will be referred to as mono-(2-methacryloyloxyl)-ethyl succinate N-hydroxysuccinimide ester or MOES-NHS.

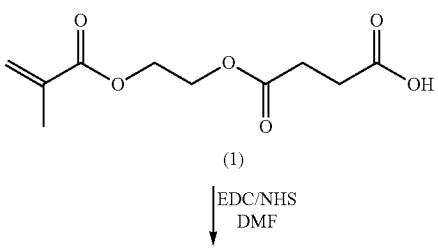

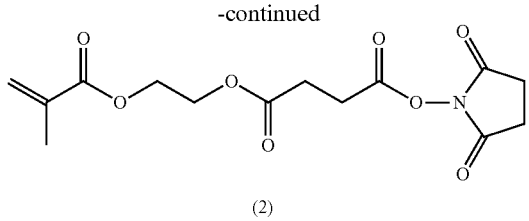

(2)

Figure 2:
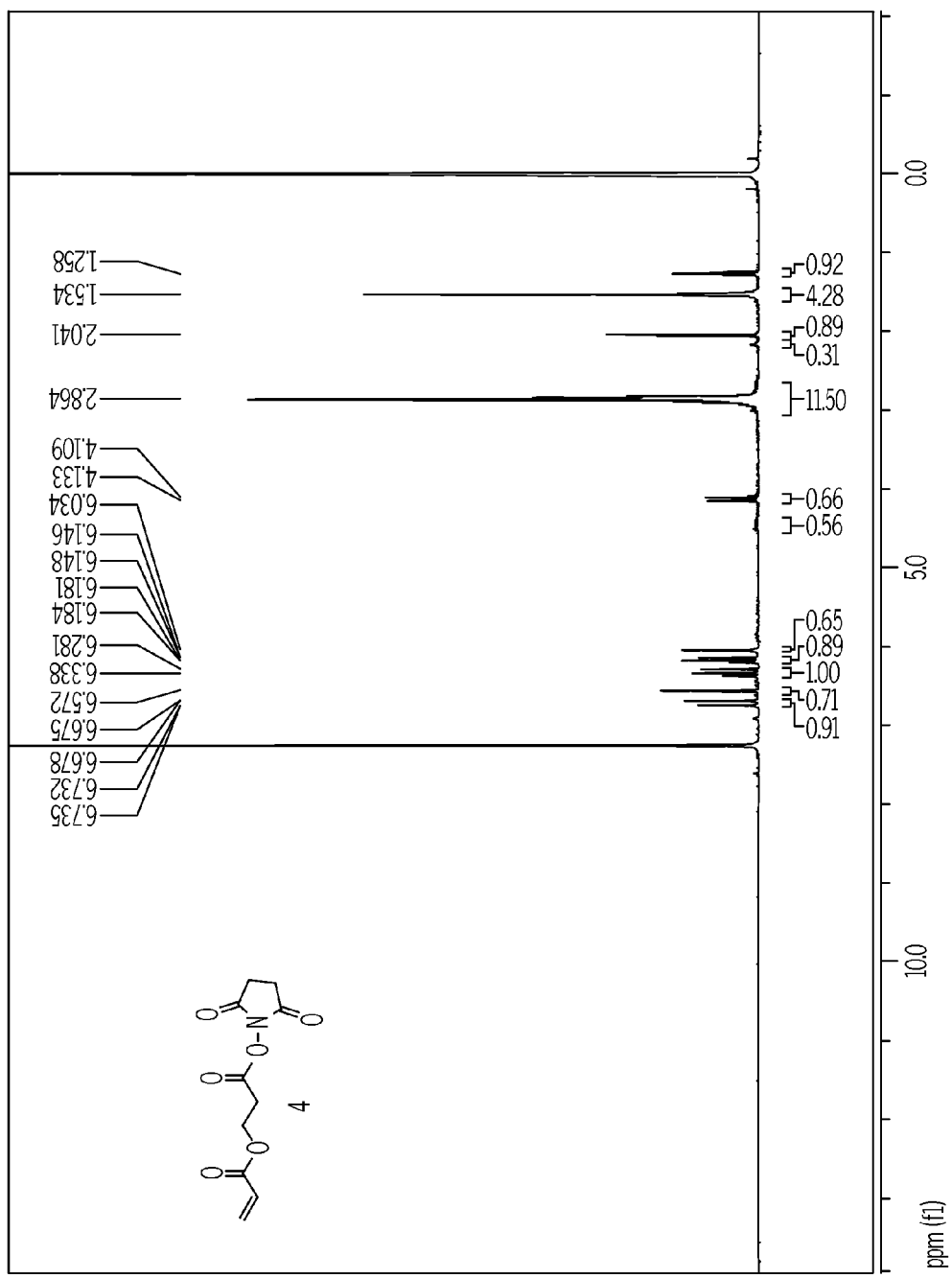
FIG. 2 is an NMR spectra of 2-carboxyethyl acrylate N-hydroxysuccinimide ester (CEA-NHS) ester, compound 4.

In an additional embodiment, a reactive NHS acrylate monomer was synthesized by the 1-(3-dimethylaminopropyl)-3-ethyl-carbodiimide hydrochloride (EDC)-mediated esterification of 2-carboxyethyl acrylate (3) (and derivatives thereof) with NHS, yielding the corresponding NHS ester (4). Compound (4) is, according to IUPAC naming conventions, 4-(2,5-dioxopyrrolidin-1-yl)-3-oxobutyl prop-2-enoate. This compound may also be called 4-(2,5-dioxopyrrolidin-1-yl)-3-oxobutyl acrylate or 2-carboxyethyl acrylate N-hydroxysuccinimide ester (CEA-NHS). This compound was made in moderate yields and >95% purity. The resultant compound had a chemical formula $C_{10}H_{11}NO_6$ and a molecular weight of 241.20. This was confirmed by $^1H$ NMR shown in FIG. 2. The chemical structures of EDC (5) and NHS (6) are also provided. For the purposes of this disclosure, this compound will be referred to as 2-carboxyethyl acrylate N-hydroxysuccinimide ester or CEA-NHS.

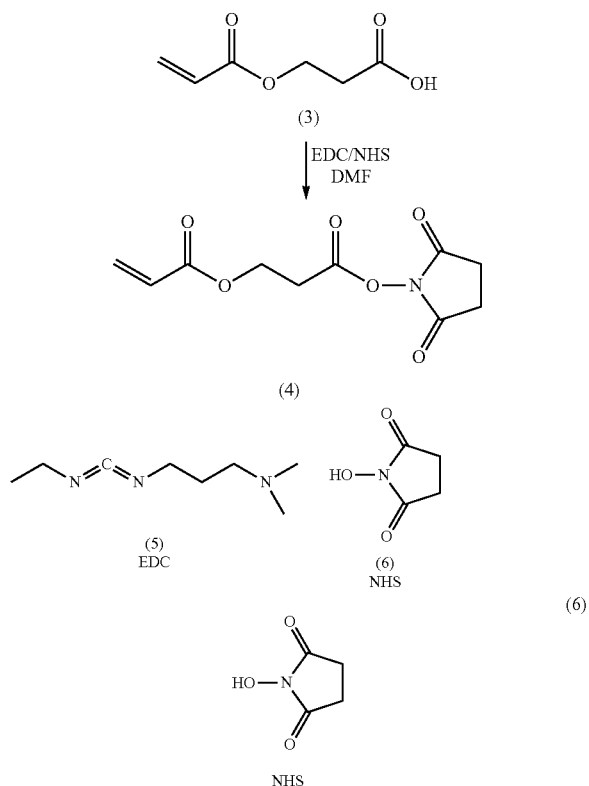

The reactive NHS acrylate monomers (2 and 4) were subsequently applied to a surface or substrate and UV cured, in combination with hydrophilic monomers (selected from compounds 7 and 8, shown in Table 1) and crosslinkers (selected from compounds 9, 10 and 11, shown in Table 2), to create synthetic polymer coated surfaces. In embodiments, peptides were conjugated to the synthetic polymer coated surfaces. Applicability of these synthetic polymer coated surfaces as cell culture surfaces was measured by culturing undifferentiated hESCs on the surfaces.

One skilled in the art of synthetic organic chemistry could generate new moderate chain length NHS acrylate or acrylamide monomers that are similar to compounds 2 and 4. For example, by a two step reaction, a "polymerizable" acrylate or methacrylate group can be introduced to a primary alcohol or amine group of a short chained compound that has both carboxylic acid and amine or carboxylic acid and alcohol groups (with the carboxylic acid group protected or unprotected) and further derivatized with N-hydroxysuccinimide. Reagents suitable for introducing the acrylate group include acryloyl chloride or (meth)acryloyl chloride, acrylic anhydride or methacrylic anhydride. Examples of short chained compounds that have both carboxylic acid and amine or carboxylic acid and alcohol groups include 6-aminohexanoic acid, L-canavanine, 4-amino-3-phehyl-butyric acid, diaminobutanoic acid derivatives such as Z-Dab-OH, (N-Boc-β-amino)-Alanine-OH, (S)-(+)-2-amino-3-(2-aminoethoxy) propanoic acid monohydrochloride, 2-amino-2-norbornanecarboxylic acid. Additionally, branched or hyperbranched versions of the N-hydroxysuccinimide acrylate monomers could be similarly synthesized from amino acids such as lysine or polylysine, and branched compounds such as poly(glutamic acid) or NaNa-bis(carboxymethyl)-L-lysine hydrate.

Figure 3A:
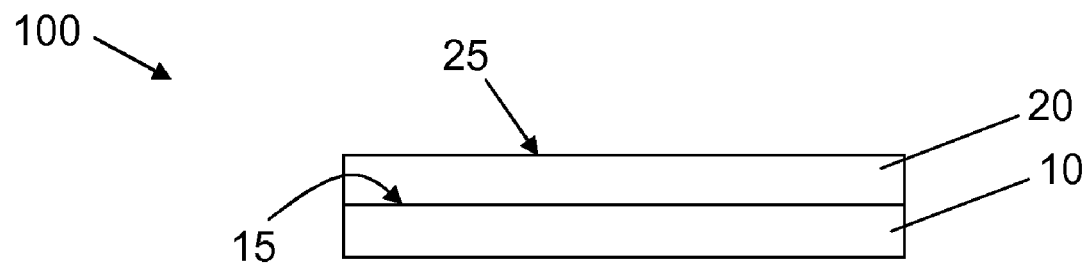
FIGS. 3A and 3B are schematic diagrams of side views of synthetic polymer layer coated articles.

Referring to FIG. 3, a schematic diagram of article 100 for culturing cells is shown. The article 100 includes a cell culture substrate or base material substrate 10 having a surface 15. A synthetic polymer coating layer 20 is disposed on the surface 15 of the cell culture substrate or base material 10. While not shown, it will be understood that synthetic polymer coating 20 may be disposed on a portion of cell culture substrate or base material 10. The cell culture substrate or base material 10 may be any material suitable for culturing cells, including ceramic, glass, glass-ceramic, metal, plastic, polymer or co-polymer, any combinations thereof, or a coating of one material on another. Such base materials 10 include glass materials such as soda-lime glass, pyrex glass, vycor glass, quartz glass, or the like. For example, substrates may be gas permeable or gas impermeable polymeric substrates or membranes made of suitable materials that may include for example: polystyrene, polyethylene, polyethyleneterephthalate, polyethylene-co-vinyl acetate, nylon, polycarbonate, polyolefin, ethylene vinyl acetate, polypropylene, polysulfone, polytetrafluoroethylene (PTFE) or compatible fluoropolymer, silicone rubber or copolymer, polystyrene-butadiene-styrene), dendritic polymers, such as poly(vinyl chloride), poly(vinyl alcohol), poly(methyl methacrylate), poly(vinyl acetate-maleic anhydride), poly(dimethylsiloxane) monomethacrylate, cyclic olefin polymers, fluorocarbon polymers, polystyrenes, polypropylene, polyethyleneimine; copolymers such as poly(vinyl acetate-co-maleic anhydride), polystyrene-co-maleic anhydride), poly(ethylene-co-acrylic acid) or derivatives of these or the like.

The substrate may be treated to alter the surface characteristics of the substrate in order for surfaces to facilitate sustainable adhesion between thermoplastic substrates and said (meth)acrylate components. For example, the substrate may be plasma treated, chemically treated, heat treated, mechanically etched, or have increased charged chemical groups available at the surface of the polymer substrate in which (meth)acrylate coating is to be applied.

In an embodiment, the substrate may be a plasma-treated polystyrene, polyolefin or cyclic olefin co-polymer surface. The plasma-treated cyclic olefin co-polymer (cyclic norbonene-ethylene) surface may be, for example, that material sold under the name of TOPAS® by Topas Advanced Polymers, Florence, Ky. In embodiments, the (meth)acrylate cell culture surface or polymer mixture can be applied to a substrate using methods known in the art, including dip coating, spray coating, spin coating, or liquid dispensing.

In embodiments, the substrate may form part of a cell culture article. Cell culture articles 100 are containers suitable for containing cells in culture. Cell culture articles include flasks, bottles, plates, single and multi-well plates such as 6, 12, 96, 384, and 1536 well plates, multi-layer flasks, jars, dishes, beakers, roller bottles, slides including chambered and multi-chambered culture slides, tubes, cover slips, membranes, cell culture container inserts, beads, fibers, hollow fibers, bags, bioreactors, fermenters, perfusion chambers, cups, spinner flasks, spinner bottles, and/or any type of cell culture vessel or container known in the art.

While all sizes are contemplated, in embodiments of the present invention, the (meth)acrylate cell culture surface covers a surface of the cell culture article that is larger than a small spot, or microspot, or larger than 1000 µm in diameter, in the cell culture article. In embodiments, the (meth)acrylate cell culture surface of the present invention covers an entire cell culture surface in the cell culture container or vessel. For example, in embodiments, the (meth)acrylate cell culture surface of the present invention covers the bottom, the cell culture growth surface, of a well of a 96-well plate. Or, in embodiments, the cell culture surface of the present invention covers the cell culture growth surface of a standard cell culture flask. Those of ordinary skill will recognize that embodiments of the present invention may provide cell culture surfaces for known cell culture vessels and containers. Synthetic polymer coating 20 provides a surface 25 on which cells may be cultured or screened. Synthetic polymer coating may be referred to as synthetic polymer layer, synthetic polymer coating, synthetic polymer surface synthetic surface or any other suitable term. In embodiments, synthetic polymer layer is formed from a hydrophilic monomer, a carboxyl group containing monomer which has been modified to attach an N-hydroxysuccinimide group (NHS) (for example compounds 2 and 4), and a crosslinking monomer. In embodiments, the carboxyl group containing monomer which has been modified to attach an N-hydroxysuccinimide group (NHS) is called a conjugator monomer.

In embodiments, examples of a hydrophilic monomer include 2-hydroxyethylmethacrylate (HEMA) or glycerol monomethacrylate (mixed isomers) (structures shown in Table 1). Examples of an N-hydroxysuccinimide modified carboxyl group containing monomer include, for example, 2-carboxyethyl acrylate N-hydroxysuccinimide ester (CEA-NHS) or mono-(2-methacryloyloxyl)-ethyl succinate N-hydroxysuccinimide ester (MOES-NHS). Examples of cross-linking monomers include, for example, triglycerol diacrylate (glycerol 1,3-diglycerolate diacryate— TDGDDA), 3-(Acryloyloxy)-2-hydroxypropyl methacrylate (AHPMA), or tetraethylene glycol dimethacrylate (TEGDMA) (structures shown in Table 2).

In an embodiment, the synthetic polymer layer is formed from hydroxyethyl methacrylate, tetra(ethylene glycol) dimethacrylate and 2-carboxyethyl acrylate N-hydroxysuccinimide ester (CEA-NHS). In an additional embodiment, the synthetic polymer layer is formed from hydroxyethyl methacrylate, tetra(ethylene glycol) dimethacrylate and mono-(2-methacryloyloxyl)-ethyl succinate N-hydroxysuccinimide ester (MOES-NHS). Of course, any other suitable (meth)acrylate monomer may be used.

TABLE 1

Hydrophilic monomers

| Compound number | Structure | Name |
|---|---|---|
| 7 | [structure] | 2-hydroxyethyl acrylate (HEMA) |
| 8 | [structure] | glycerol monomethacrylate (mixed isomers) (GMMA) |

TABLE 2

Cross-linkers

| Compound number | Structure | Name |
|---|---|---|
| 9 | [structure] | triglycerol diacrylate (glycerol 1,3-diglycerolate diacryate) (TDGDDA) |
| 10 | [structure] | 3-(Acryloyloxy)-2-hydroxypropyl methacrylate (AHPMA) |
| 11 | [structure] | tetra-ethyleneglycol dimethacrylate (TEGDMA) |

Figure 3B:
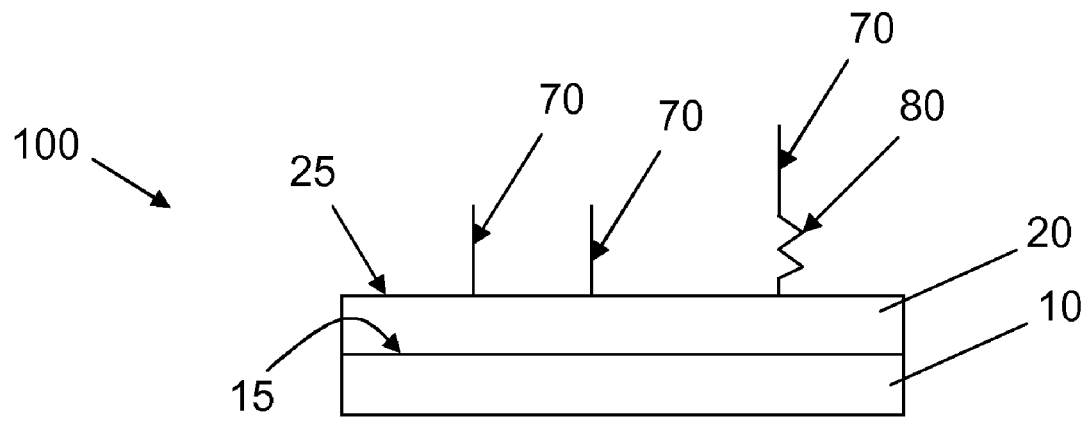

Referring now to FIG. 3B, other materials, such as bioactive compound 70, may be incorporated into or conjugated to synthetic polymer surface 20, e.g. to produce a biomimetic surface. In embodiments, the bioactive compound is a polypeptide, or peptide or protein and is conjugated to the synthetic polymer surface Referring now to FIG. 1C, other materials, such as bioactive compounds 70, may be incorporated into or conjugated to synthetic polymer surface 20, e.g. to produce a biomimetic surface. In embodiments, the bioactive compound is a protein, a polypeptide (or peptide). For the purposes of this disclosure, the terms polypeptide and peptide are synonymous. For example the bioactive compound may be a molecule capable of binding noncovalently to specific and complimentary portions of molecules or cells. Examples of such bioactive compounds include cell surface receptors which bind to ligands, antigens which bind to antibodies.

In embodiments, larger proteins may be conjugated to synthetic polymer surface. Proteins may include both animal derived or non-animal derived recombinant proteins. Recombinant proteins may be sourced from bacterial plasmid expression systems, eukaryotic expression systems such as baculovirus. It is also contemplated that protein-sourcing from cell-free expression systems such as the RTS Wheat germ cell-free synthesis process (available from Roche, Inc.) may also be applied.

In additional embodiments, larger proteins may be conjugated to the pre-activated derivatized surface. In embodiments, large proteins may be conjugated to the derivatized surface in aqueous conditions. Alternatively, one can also use hapten binding retention of hapten tagged proteins. It is know in the art that biotinylated proteins can be retained with high selectivity via Streptavidin and Avidin complexes. A protein may be tagged with biotin by either chemical or enzymatic processes. The AviTag® process by GeneCopoeia Inc. involves fusion of a biotin linker using biotin ligase.

In embodiments, the protein to be attached may be extracellular matrix proteins, such as, for example, Collagen Type 1, II, III, IV, V, VI, VII, VIII, Fibronectin, vitronectin, Laminin a, b and c chains Enactin, Elastin and any other ECM proteins. Glycoproteins and growth factors may also be attached to the synthetic polymer surface.

In embodiments, bioactive compounds may be conjugated to the synthetic polymer surface via the NHS-moiety of the conjugator monomer (for example, compounds 2 and 4). A linker or spacer 80, such as a repeating polyethylene glycol linker or any other suitable linker, may be conjugated to the NHS moiety of the conjugator monomer, and then attached to a polypeptide. In embodiments, the linker or space may be used to increase distance from bioactive compound 70 to surface 25 of synthetic polymer layer 20. All, some, or none of the polypeptides 70 may be conjugated to synthetic polymer layer 20 via linkers 80.

Other materials, such as bioactive compounds 70, may be incorporated into or conjugated to synthetic polymer surface 20, e.g. to produce a biomimetic surface. In embodiments, the bioactive compound is a protein, a polypeptide (or peptide). For the purposes of this disclosure, the terms polypeptide and peptide are synonymous. For example the bioactive compound may be a molecule capable of binding noncovalently to specific and complimentary portions of molecules or cells. Examples of such bioactive compounds include cell surface receptors which bind to ligands, antigens which bind to antibodies.

Where the bioactive compound 70 is a polypeptide, the polypeptide may be conjugated to the synthetic polymer layer 20 at any density, preferably at a density suitable to support culture of cells for a desired purpose. For example, polypeptide 70 may be conjugated to synthetic polymer layer 20 at a density of between about 1 pmol per $mm^2$ and about 50 pmol per $mm^2$ of surface 25 of synthetic polymer layer 20, which can be estimated by the area of surface 15 of base material substrate 10 that is coated in embodiments where surface 15 is uniformly coated by synthetic polymer layer 20. For example, the polypeptide may be present at a density of greater than 5 pmol/$mm^2$, greater than 6 pmol/$mm^2$, greater than 7 pmol/$mm^2$, greater than 8 pmol/$mm^2$, greater than 9 pmol/$mm^2$, greater than 10 pmol/$mm^2$, greater than 12 pmol/$mm^2$, greater than 15 pmol/$mm^2$, or greater than 20 pmol/$mm^2$ of the surface of the synthetic polymer layer 20. It will be understood that the amount of polypeptide 70 present can vary depending on the composition of the synthetic polymer layer 20, the thickness of the synthetic polymer layer 20 and the nature of the polypeptide 70 itself.

In various embodiments, the polypeptide is derived from a naturally occurring cell adhesion polypeptide, such as fibronectin, laminin, vitronectin, or the like. In some embodiments, the polypeptide contains an RGD amino acid sequence. In embodiments, the polypeptide is KGGNGEPRGDTYRAY (SEQ ID NO:1) which is an RGD sequence from bone sialoprotein with an additional "KGG" sequence is added to the N-terminus. Lysine (K) was used for chemical conjugation, and two glycine amino acids (GG) were added as spacers. In additional embodiments cystine (C) may be used for chemical conjugation. In embodiments, a conjugation and spacer sequence (KGG or CGG, for example) may be present or absent. In additional embodiments, the polypeptide may be, for example, NGEPRGDTYRAY, (SEQ ID NO:2), GRGDSPK (SEQ ID NO:3) (short fibronectin) AVTGRGDSPASS (SEQ ID NO:4) (long FN), PQVTRGDVFTMP (SEQ ID NO:5) (vitronectin), RNIAEIIKDI (SEQ ID NO:6) (lamininβ1), KYGRKRLQVQLSIRT (SEQ ID NO:7) (mLMα1 res 2719-2730), NGEPRGDTRAY (SEQ ID NO:8) (BSP-Y), NGEPRGDTYRAY (SEQ ID NO:9) (BSP), KYGAASIKVAVSADR (SEQ ID NO:10) (mLMα1 res 2122-2132), KYGKAFDITYVRLKF (SEQ ID NO:11) (mLMγ1 res 139-150), KYGSETTVKYIFRLHE (SEQ ID NO:12) (mLMγ1 res 615-627), KYGTDIRVTLNRLNTF (SEQ ID NO:13) (mLMγ1 res 245-257), TSIKIRGTYSER (SEQ ID NO:14) (mLMγ1 res 650-261), TWYKIAFQRNRK (SEQ ID NO:15) (mLMα1 res 2370-2381), SINNNRWHSIYITRFGNMGS (SEQ ID NO:16) (mLMα1 res 2179-2198), KYGLALERKDHSG (SEQ ID NO:17) (tsp1 RES 87-96), GQKCIVQTTSWSQCSKS (SEQ ID NO:18) (Cyr61 res 224-240).

In additional embodiments, the peptide comprises KGGK$^4$DGEPRGDTYRATD$^{17}$ (SEQ ID NO:19), where Lys$^4$ and Asp$^{17}$ together form an amide bond to cyclize a portion of the polypeptide; KGGL$^4$EPRGDTYRD$^{13}$ (SEQ ID NO:20), here Lys$^4$ and Asp$^{13}$ together form an amide bond to cyclize a portion of the polypeptide; KGGC$^4$NGEPRGDTYRATC$^{17}$ (SEQ ID NO:21), where Cys$^4$ and Cys$^{17}$ together form a disulfide bond to cyclize a portion of the polypeptide; KGGC$^4$EPRGDTYRC$^{13}$ (SEQ ID NO:22), where Cys$^4$ and Cys$^{13}$ together form a disulfide bond to cyclize a portion of the polypeptide, or KGGAVTGDGNSPASS (SEQ ID NO:23). In embodiments, the polypeptide may be acetylated or amidated or both. While these examples are provided, those of skill in the art will recognize that any peptide or polypeptide sequence may be conjugated to embodiments of the synthetic polymer coating of the present invention.

Synthetic polymer coating layer 20 may have any desirable thickness. However, it has been found that thicker coatings, e.g. coatings of greater than about 10 micrometers, tend to have unevenness around the periphery of the coating due to surface tension. In various embodiments, the thickness of the coating layer 20 is less than about 10 micrometers. For example, the thickness may be less than about 5 micrometers, less than about 2 micrometers, less than about 1 micrometers, less than about 0.5 micrometers or less than about 0.1 micrometers.

The polymer material forming synthetic polymer layer 20 may be cross-linked to any suitable degree. Low degree of crosslinking may result in partial or complete synthetic polymer layer dissolution and lower polymerization reaction efficiency. In various embodiments, the crosslinking density of synthetic polymer layer 20 is between about 0.9% and about 9%.

Of course, the surface 25 may be of any suitable size. However, when the area of the surface 15 is too small, reliable cell responses may not be readily observable because some cells, such as human embryonic stem cells, are seeded as colonies or clusters of cells (e.g., having a diameter of about 0.5 mm) and adequate surface area is desirable to ensure attachment of sufficient numbers of colonies to produce a quantitative cell response. In numerous embodiments, an article 100 has a well 50 having a uniformly coated surface 15, where the surface 15 has an area greater than about 0.1 cm$^2$, greater than about 0.3 cm$^2$, greater than about 0.9 cm$^2$, or greater than about 1 cm$^2$.

In various embodiments, the synthetic polymer layer may be attached to a surface of a cell culture article. For the purposes of this disclosure, "attached" means coated on or layered on a base material or substrate so that the synthetic polymer layer does not delaminate from the base material upon exposure to normal cell culture conditions including exposure to aqueous media. The synthetic polymer layer may be attached to the substrate via covalent or non-covalent interactions. Examples of non-covalent interactions that may associate the synthetic SA surface with the substrate include chemical adsorption, hydrogen bonding, surface interpenetration, ionic bonding, van der Waals forces, hydrophobic interactions, dipole-dipole interactions, mechanical interlocking, and combinations thereof. Examples of covalent interactions may include copolymerization of the (meth)acrylate monomers with a surface containing either a polymerizable group (e.g., acrylate), a group capable of fragmenting to produce free radical, or chain transfer agent, and combinations thereof.

For the purposes of this disclosure, the term "(meth)acrylate" means compounds that are esters which contain vinyl groups, that is, two carbon atoms double bonded to each other, directly attached to a carbonyl carbon. An acrylate moiety is a moiety of the following formula: $CH_2CHC(O)O^-$. Some acrylates, methacrylates, have an extra methyl group attached to the α-carbon and these are also included in the term "(meth)acrylate" for the purposes of this disclosure. A methacrylate moiety is a moiety of the following formula: $CH_2C(CH_3)C(O)O^-$. "acrylate" and "(meth)acrylate" are used herein interchangeably, except when content clearly dictates otherwise, e.g. when a specific compound or group of compounds are named. "(meth)acrylate" includes compounds which contain single (meth)acrylate groups or multiple (meth)acrylate groups. "(meth)acrylate" includes acrylates and methacrylates as well as polymerized and unpolymerized monomers (oligomers) with varying reactive functionality, that is, dimers, trimers, tetramers or additional polymers containing acrylic or methacrylic acid groups. "UV-curable monomers," for the purposes of this disclosure means monomers that can be cross-linked to form polymers by exposure to UV light, heat or other initiator system.

2. Coating of Synthetic Polymer Layer

The discussion that follows makes reference to articles 100 and components thereof as described above with regard to FIGS. 3A and 3B. However, it will be understood that any suitable article may be employed with regard to the methods that follow.

Figure 4:
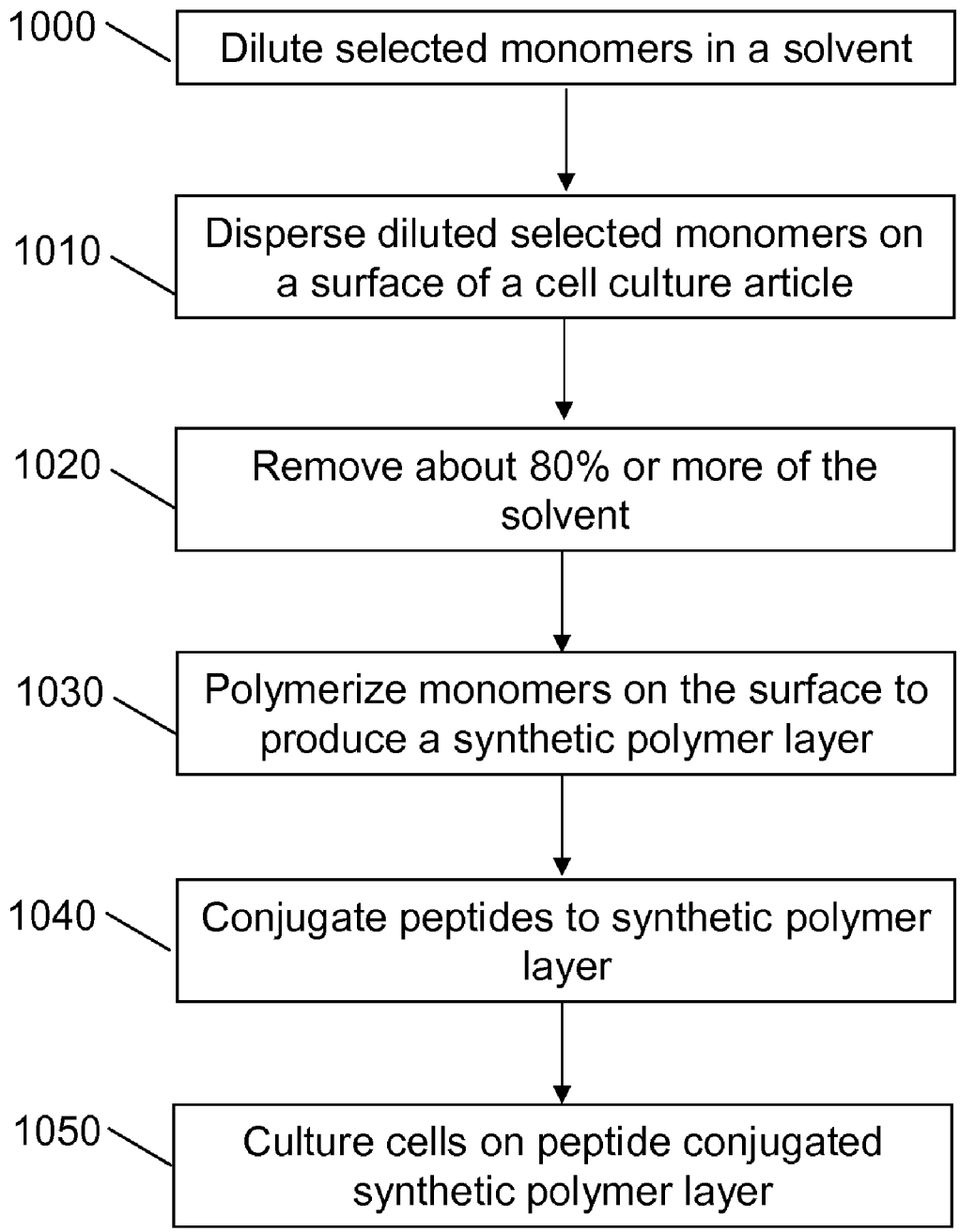
FIG. 4 is a flow diagram of representative method for producing a cell culture article having a synthetic polymer layer.

Referring now to FIG. 4, a flow diagram of a method for producing a cell culture article is shown. The method includes (1000) diluting one or more monomers in a solvent and (1010) dispersing the diluted monomers on a surface 15 of a cell culture article 100. About 80% or more of the solvent is then removed in step (1020). After removing the solvent the monomers are polymerized on the surface 15 of the article 100 in situ in step (1030). In some embodiments, about 90% or more, about 95% or more, about 99% or more, substantially all, or essentially all of the solvent is removed prior to polymerizing the monomers. After the monomers are polymerized in step 1030 to form polymers, peptides are conjugated to the polymers (1040). In an additional step, in embodiments, cells may be grown on the peptide conjugated synthetic polymer layer (1050).

Any suitable solvent may be used in the process of forming the synthetic polymer layer depicted in FIG. 4, steps 1010-1030. In various embodiments, the solvent is a volatile solvent. As used herein, a volatile solvent is a solvent having a boiling point of less than about 120° C., less than about 100° C., less than about 90° C., or less than about 85° C. For example, the volatile solvent may have a boiling point between about 34° C. and about 120° C., between about 50° C. and about 100° C., or between about 70° C. and about 85° C. Examples of volatile solvents include acetone, methanol, ethyl acetate, ethanol, butanone, acetonitrile, 2-propanol, and 2-butanol. A volatile solvent preferably is readily evaporatable at room temperature, compatible with the monomers used to generate the synthetic polymer surface, non-interfering with free-radical polymerization, and non-toxic to cells to be cultured. A volatile solvent may include a non-volatile component, such as dimethyl formamide or dimethyl sulfoxide. When a volatile solvent includes a non-volatile component, the non-volatile component is preferably kept to an amount of less than about 10% by volume. A solvent used in accordance with a method as described herein is preferably a poor solvent for the base material 10 of the culture ware article 100.

A representative example of suitable class of volatile solvents is ethanol solvents. As used herein, "ethanol solvent" means a solvent having greater than about 75% ethanol. For example, an ethanol solvent may contain greater than 80%, greater than 90%, greater that 95%, greater than 97%, or greater than 99% ethanol. In various embodiments, the ethanol solvent consists essentially of ethanol. In some embodiments, an ethanol solvent consists essentially of ethanol and water. The use of an ethanol solvent may provide one or more advantages over the use of no solvent. For example, use of an ethanol solvent reduces monomer viscosity, making it possible to use automated instrumentation in the formulation process. Efficiency has been increased ten fold relative to use of no solvent, making it possible to do high throughput material screening. Use of an ethanol solvent promotes monomer spreading to achieve a thin and uniform coating for small or large surface areas using automated liquid handling instrumentation and increases coating efficiency. Use of an ethanol solvent also reduces the amount of monomer used for the coating process and may reduce final coating thickness. This can reduce cost by reducing consumption of monomers while reducing stress in coating during polymerization and swelling after contact with culture medium and finally reduces coating de-lamination. Compared to other solvents, ethanol solvents are more likely to be safe for the manufacture of cell culture ware for therapeutic cells or tissues, as ethanol solvents have been used in biomedical and pharmaceutical processes. Further, ethanol solvents are commercially available in USP grade, are easy to evaporate or otherwise remove during coating process without extreme conditions such as extreme vacuum or heat, are good solvents for a large majority of (meth)acrylate monomers while being a poor solvent form many polymers used in cell culture ware base material. In addition, ethanol appears to be relatively inert during free radical polymerization. Therefore, side effects of an ethanol solvent on the subsequent polymerization of the coating have been found to be minimal. 2-propanol solvents share many of the above-described advantages of ethanol solvents.

The monomers may be diluted with solvent by any suitable amount to achieve the desired viscosity and monomer concentration. Generally the monomer compositions used according to the teachings presented herein contain between about 0.1% to about 99% monomer. By way of example, the monomer may be diluted with an ethanol solvent to provide a composition having between about 0.1% and about 50% monomer, from about 0.01% to about 10% monomer by volume, from about 0.1% to about 5% monomer by volume, or from about 0.1% to about 1% monomer by volume. The monomers may be diluted with solvent so that the polymer layer 20 achieves a desired thickness. As discussed above, if the deposited monomers are too thick, a non-uniform surface may result and the coating may likely de-laminate after contact with an aqueous medium.

In various embodiments, synthetic polymer surface 20 is produced by depositing one or more monomers on a surface 15 of a base material 10 and then polymerizing the one or more monomers in situ. The synthetic polymer surface 20 may be associated with the base material surface 15 via covalent or non-covalent interactions. Examples of non-covalent interactions that may associate the synthetic polymer surface with the substrate include chemical adsorption, hydrogen bonding, surface interpenetration, ionic bonding, van der Waals forces, hydrophobic interactions, dipole-dipole interactions, mechanical interlocking, and combinations thereof.

Cells in culture, including embryonic stem cells and human embryonic stem cells, require medium. Research in the area of synthetic substrates has claimed positive results using medium supplemented with serum replacement and conditioned with mouse embryonic fibroblasts (MEFs) (Li, J. Ying, Chung, E. H., Rodriguez, Firpo, M. T., Healy, K. E., Hydrogels as Artificial matrices for Human Embryonic Stem Cell Self-Renewal, Journal of Biomedical Materials Research part A, Jun. 1, 2006, volume 79A, Issue 1, pp 1-5C). Chemically defined medium, medium in which all components are known is available from a number of vendors including, for example, Stem Cell Technologies, Invitrogen, Carlsbad Calif., and Millipore, Boston, Mass. In order to facilitate growth of a particular cell type, including undifferentiated hESC cells, as well as differentiation into particular cell types, additives such as growth factors may be added to the chemically defined media. These growth factors may include but are not limited to transforming growth factor-alpha (TGF-alpha), transforming growth factor-beta. (TGF-beta), platelet-derived growth factors including the AA, AB and BB isoforms (PDGF), fibroblast growth factors (FGF), including FGF acidic isoforms 1 and 2, FGF basic form 2, and FGF 4, 8, 9 and 10, hbFGF, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor (HGF), glial neurotrophic growth factor (GDNF), stem cell factor (SCF), keratinocyte growth factor (KGF), transforming growth factors (TGF), including TGFs alpha, beta, beta1, beta2, and beta3, skeletal growth factor, bone matrix derived growth factors, and bone derived growth factors and mixtures thereof. Some growth factors can also promote differentiation of a cell or tissue. TGF, for example, can promote growth and/or differentiation of a cell or tissue. Some preferred growth factors include VEGF, NGFs, PDGF-AA, PDGF-BB, PDGF-AB, FGFb, FGFa, hbFGF, HGF, and BGF. Medium may be conditioned, or exposed to a feeder layer of cells. In addition, serum may be added to the media. Fetal bovine serum, FBS is available from many sources including Hyclone and Sigma-Aldrich. For the purposes of the experiments described herein, X-Vivo-10 serum-free media from Lonza, Basel, Switzerland was used, amended with the addition of 80 ng/ml hbFGF and 0.5 ng/ml hTGF-β1, and included at least 20% FBS.

Stem cells include adult and embryonic stem cells. Human Embryonic cells in cell lines include CH01, CH02, CY12, CY30, CY40, CY51, CY81, CY82, CY91, CY92, CY10, GE01 (WA01, also known as H1), GE07 (WA07, H7), GE09 (WA09, H9), GE13, GE14, GE91, GE92, SA04-SA19, KA08, KA09, KA40, KA41, KA42, KA43, MB01, MB02, MB03, MI01, NC01, NC02, NC03, RL05, RL07, RL10, RL15, RL20, RL21, as well as numerous others. Stem cells may also be primary cells obtained from embryonic sources, such as surplus in vitro fertilized eggs. Examples of stem cells include, but are not limited to, embryonic stem cells, bone marrow stem cells and umbilical cord stem cells. Induced primate pluripotent stem (iPS) cells may also be used. iPS cells refer to cells, obtained from a juvenile or adult mammal, such as a human, that are genetically modified, e.g., by transfection with one or more appropriate vectors, such that they are reprogrammed to attain the phenotype of a pluripotent stem cell such as an hESC. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm and thus are suitable for differentiation into OPCs. The iPS cells, like hESC, also form teratomas when injected into immuno-deficient mice, e.g., SCID mice. (Takahashi et al., (2007) Cell 131(5):861; Yu et al., (2007) Science 318:5858). Other examples of cells used in various embodiments include, but are not limited to, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, and neurons. In one aspect, bone cells such as osteoclasts, osteocytes, and osteoblasts can be cultured with the coated substrates produced herein. Cells useful herein can be cultured in vitro, derived from a natural source, genetically engineered, or produced by any other means. Any source of cells can be used. Atypical or abnormal cells such as tumor cells can also be used herein. Cells that have been genetically engineered can also be used. Engineering involves programming the cell to express one or more genes, repressing the expression of one or more genes, or both. Genetic engineering can involve, for example, adding or removing genetic material to or from a cell, altering existing genetic material, or both. Embodiments in which cells are transfected or otherwise engineered to express a gene can use transiently or permanently transfected genes, or both. Gene sequences may be full or partial length, cloned or naturally occurring.

In the examples presented here, H1 (or WA01, or GE01) cells are used. However, it is contemplated that any cells, including stem cells or hESC may exhibit preferable characteristics when cultured on embodiments of the cell culture surfaces of the present invention.

3. Culturing Cells on Peptide-Conjugated Synthetic Polymer Layer

A substrate coated with a synthetic polymer layer 20 as described above may be giving rise to a fully differentiated or mature cell types. A stem cell may be a bone marrow-derived stem cell, autologous or otherwise, a neuronal stem cell, or an embryonic stem cell. A stem cell may be nestin positive. A stem cell may be a hematopoietic stem cell. A stem cell may be a multi-lineage cell derived from epithelial and adipose tissues, umbilical cord blood, liver, brain or other organ.

Because human embryonic stem cells (hESC) have the ability to grow continually in culture in an undifferentiated state, the hESC for use in this invention may be obtained from an established cell line. Examples of human embryonic stem cell lines that have been established include, but are not limited to, H1, H7, H9, H13 or H14 (available from WiCell established by the University of Wisconsin) (Thompson (1998) Science 282:1145); hESBGN-01, hESBGN-02, hES-BGN-03 (BresaGen, Inc., Athens, Ga.); HES-1, HES-2, HES-3, HES-4, HES-5, HES-6 (from ES Cell International, Inc., Singapore); HSF-1, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., Fertil. Steril. 83(5):1517-29, 2005); lines HUES 1-17 (Cowan et al., NEJM 350(13):1353-56, 2004); and line ACT-14 (Klimanskaya et al., Lancet, 365(9471):1636-41, 2005). Embryonic stem cells used in the invention may also be obtained directly from primary embryonic tissue. Typically this is done using frozen in vitro fertilized eggs at the blastocyst stage, which would otherwise be discarded.

Other suitable stem cells include induced primate pluripotent (iPS) stem cells OPCs according to the invention may also be differentiated from induced primate pluripotent stem (iPS) cells. iPS cells refer to cells, obtained from a juvenile or adult mammal, such as a human, that are genetically modified, e.g., by transfection with one or more appropriate vectors, such that they are reprogrammed to attain the phenotype of a pluripotent stem cell such as an hESC. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm and thus are suitable for differentiation into a variety of cell types. The iPS cells, like hESC, also form teratomas when injected into immuno-deficient mice, e.g., SCID mice. (Takahashi et al., (2007) Cell 131(5):861; Yu et al., (2007) Science 318:5858).

Prior to seeding cells, the cells may be harvested and suspended in a suitable medium, such as a growth medium in which the cells are to be cultured once seeded onto the surface. For example, the cells may be suspended in and cultured in serum-containing medium, a conditioned medium, or a chemically-defined medium. As used herein, "chemically-defined medium" means cell culture media that contains no components of unknown composition. Chemically defined media may, in various embodiments, contain no proteins, hydrosylates, or peptides of unknown composition. In some embodiments, chemically-defined media contains polypeptides or proteins of known composition, such as recombinant growth hormones. Because all components of chemically-defined media have a known chemical structure, variability in culture conditions and thus cell response can be reduced, increasing reproducibility. In addition, the possibility of contamination is reduced. Further, the ability to scale up is made easier due, at least in part, to the factors discussed above. Chemically defined cell culture media are commercially available from, for example, Invitrogen (Invitrogen Corporation, 1600 Faraday Avenue, PO Box 6482, Carlsbad, Calif. 92008) as StemPro® a fully defined, serum- and feeder-free medium (SFM) specially formulated for the growth and expansion of human embryonic stem cells (hESCs), StemCell Technologies, Inc as mTeSR™1 maintenance media for human embryonic stem cells and XVivo-10, which can be supplemented with growth factors, available from Lonza.

One or more growth or other factors may be added to the medium in which cells are incubated with the synthetic polymer layer 20. The factors may facilitate cellular proliferation, adhesion, self-renewal, differentiation, or the like. Examples of factors that may be added to or included in the medium include muscle morphogenic factor (MMP), vascular endothelium growth factor (VEGF), alpha or beta transforming growth factor (TGF), interleukins, nerve growth factor (NGF), erythropoietin, platelet derived growth factor (PDGF), epidermal growth factor (EGF), activin A (ACT), such as Activin A, hematopoietic growth factors, retinoic acid (RA), interferons, fibroblastic growth factors (FGF), such as basic fibroblast growth factor (bFGF), bone morphogenetic protein (BMP), peptide growth factors, heparin binding growth factor (HBGF), hepatocyte growth factor (HGF), tumor necrosis factors (TNF), insulin-like growth factors (IGF) I and II, transforming growth factors (TGF), such as transforming growth factor-$\beta 1$ (TGF$\beta 1$), and colony stimulating factors.

The cells may be seeded at any suitable concentration. Typically, the cells are seeded at about 10,000 cells/cm$^2$ of substrate to about 500,000 cells/cm$^2$. For example, cells may be seeded at about 40,000 cells/cm$^2$ of substrate to about 150,000 cells/cm$^2$. However, higher and lower concentrations may readily be used. The incubation time and conditions, such as temperature, $CO_2$ and $O_2$ levels, growth medium, and the like, will depend on the nature of the cells being cultured and can be readily modified. The amount of time that the cells are incubated on the surface may vary depending on the cell response being studied or the cell response desired.

In general, the cell culture surfaces, synthetic polymer surfaces, were made from the combinations of conjugator monomers, hydrophilic monomers and cross-linker monomers where the conjugator monomers were mono-(2-methacryloyloxyl)-ethyl succinate N-hydroxysuccinimide ester (MOES-NHS) or 2-carboxyethyl acrylate N-hydroxysuccinimide ester (CEA-NHS), the hydrophilic monomers were as shown in Table 1 and the cross-linker monomers were as shown in Table 2. The monomers were first mixed in appropriate proportions of monomers as defined below in a solution containing a photo-initiator and a solvent. The mixture was applied to a 96 well plate and distributed the over the surface of the well. The solvent was allowed to evaporate. The monomers were cross-linked using a UV light source. This method produces a polymer surface, but not an interpenetrating network. Peptides were then conjugated to the synthetic polymer surface. Cells were then cultured, in suitable media, on the surfaces. Quality of cell growth, or the undifferentiated hESC attachment and proliferation on embodiments of (meth)acrylate surfaces of the present invention, was assessed by comparing the morphology of undifferentiated proliferating H1 hESC cells, including cell size, shape, and the interactions of one cell with another cell on the cell culture surfaces of the present invention with H1 hESC cells grown on Matrigel™.

The following examples are included to demonstrate embodiments of the invention and are not intended to limit the scope of the invention in any way. It should be appreciated by those of skill in the art that the techniques disclosed in the examples which follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of NHS-Derivatized Monomers

Abbreviations: CEA-NHS—2-carboxyethyl acrylate N-hydroxysuccinimide ester, CEMA—2-carboxyethyl methacrylate, MOES-NHS-mono-(2-methacryloyloxyl)-ethyl succinate N-hydroxysuccinimide ester, DMF—N,N'-dimethylformamide, EDC—1-(3-dimethylaminopropyl)-3-ethyl-carbodiimide hydrochloride, TEGDMA—tetraethyleneglycol dimethacrylate, EtOAC—ethyl acetate, HCl—hydrochloric acid, HEMA—2-hydroxyethyl methacrylate, NHS—N-hydroxysuccinimide, NMR—nuclear magnetic resonance, $NaHCO_3$—sodium bicarbonate, $Na_2SO_4$—anhydrous sodium sulfate, PBS—phosphate buffered sailine.

General Procedures. Solution reactions were carried out at 25° C. in glass round-bottomed flask and mixed by magnetic stirrer, unless indicated otherwise. All starting materials and solvents were reagent grade from Sigma-Aldrich (Milwaukee, Wis.), with the exception of the following: EDC was from Pierce (Rockford, Ill.); ethyl acetate and sodium bicarbonate were from Fisher Scientific (Pittsburg, Pa.). All organic phases after extractive workup were dried over anhydrous $Na_2SO_4$, following which solvent removal was performed at reduced pressures and at temperatures less than 40° C. $^1$H NMR spectra were obtained at ambient temperature and recorded at 300 MHz on a Varian VXR spectrometer.

Synthesis of mono-(2-methacryloyloxyl)-ethyl succinate N-hydroxysuccinimide ester (MOES-NHS). A solution of mono-(2-methacryoyloxyl)-ethyl succinate (12200 mg, 53.0 mmol), NHS (5870 mg, 51.0 mmol), and EDC (9590 mg, 50.0 mmol) in dry DMF (100 mL) was stirred under nitrogen for 24 h at 25° C. After dilution with ethyl acetate (250 mL), the organic layer was washed with 1 N aqueous HCl (3×250 mL), 5% aqueous $NaHCO_3$ (3×250 mL), saturated sodium chloride (1×250 mL), and then dried over anhydrous $Na_2SO_4$. The slurry was gravity filtered, concentrated and dried overnight under high vacuum to give the NHS ester as a clear colorless oil; yield 62%-75%. $^1$H NMR (300 MHZ, $CDCl_3$): δ 6.12-6.13 (m, 1H), 5.58-6.00 (dd, J=1.8 Hz, 1.7 1H), 4.34-4.42 (m, 4H), 2.96 (t, J=6.9 Hz, 2H), 2.83 (s, 4H), 2.78 (t, J=6.9 Hz, 2H), 1.95 (s, 3H).

Synthesis of 2-carboxyethyl acrylate N-hydroxysuccinimide ester (CEA-NHS). A solution of 2-carboxyethyl acrylate (680 mg, 5.30 mmol), NHS (587 mg, 5.10 mmol), and EDC (957 mg, 5.00 mmol) in dry DMF (10 mL) was stirred under nitrogen for 24 h at 25° C. After dilution with EtOAc (50 mL), the organic layer washed with 1 N aqueous HCl (3×25 mL), 5% aqueous $NaHCO_3$ (3×25 mL), brine (1×25 mL), and then dried over anhydrous $Na_2SO_4$. The slurry was gravity filtered, concentrated and dried overnight under vacuum to give the NHS ester as a clear colorless oil; yield 45%-75%. $^1$H NMR (300 MHZ, $CDCl_3$): δ 6.70 (d, J=15 Hz, 1H), 6.25-6.48 (dd, J=15.0 Hz, 9.0 1H), 6.17 (d, J=9.0 Hz, 1H), 2.80-2.92 (m, 8H).

EXAMPLE 2

Preparation of Surfaces

Photoinitiators Irgacure-819 (Phosphine oxide, phenyl bis (2,4,6-trimethyl benzoyl) and Darocur 1173 (2-hydroxy-2-methyl-1-phenyl-1-propanone) used in the free radical polymerization of the synthetic polymer formulations were obtained from Ciba Specialty Chemicals (Newport Del.) and used without any further purification. Hydrophilic crosslinkers, tetraethylene glycol dimethacrylate (86680), 3-(Acryloyloxy)-2-hydroxypropyl methacrylate (454982) and glycerol 1,3-diglycerol diacrylate (475807) were all purchased from Sigma-Aldrich in the purity as described in product specification sheet. Hydrophilic monomers 2-hydroxyethyl-methacrylate, +99% (477028) was purchased from Sigma-Aldrich while the other hydrophilic monomer used in the formulations, glycerol monomethacrylate isomers (04180) was purchased from Polysciences Incorporated without further purification. The NHS functionalized acrylate monomers mono-(2-methacryloyloxyl)-ethyl succinate N-hydroxysuccinimide ester and 2-carboxyethyl acrylate N-hydroxysuccinimide ester were synthesized as described in Example 1. Ethanol and isopropyl alcohol (available from Bio. Inc. and purchased from Sigma-Aldrich) were used as non-reactive diluents in the process.

A. Preparation of (Meth)Acrylates

Into a separate 20 ml scintillation vial quantities of 60 µL, 65 µL, 70 µL and 75 µL of 2-hydroxyethyl methacrylate was added, subsequently 40 µL, 35 µL, 30 µL, and 25 µL of the MOES-NHS or CEA-NHS esters (0.2 to 0.8 g/mL in ethanol) were added along with 30 µL of 10% of tetra(ethylene glycol) dimethacrylate, 30 µL of Darocur 1173 (10% in ethanol), 10 µL Irgacure 819 (1% in ethanol) and 9.83 ml of ethanol. This recipe amounts to a 1% formulation in ethanol. Subsequently, 40 µL of IPA was added to the entire 1% formulation. Formulations are shown in Tables 3 and 4.

TABLE 3

| HEMA | 70 µL |
|---|---|
| mono-(2-methacryoyloxyl)-ethyl succinate N-hydroxysuccinimide ester (0.2-0.8 g/mL in EtOH) | 30 µL |
| TEGMDA | 30 µL |
| Darocur 1173 (10% in EtOH) | 30 µL |
| Irgacure I-819 (1% in EtOH) | 10 µL |
| Ethanol | 9.83 mL |

TABLE 4

| HEMA | 70 µL |
|---|---|
| 2-carboxyethylacrylate N-hydroxysuccinimide ester (0.2-0.8 g/mL in EtOH) | 30 µL |
| TEGMDA | 30 µL |
| Darocur 1173 (10% in EtOH) | 30 µL |
| Irgacure I-819 (1% in EtOH) | 10 µL |
| Ethanol | 9.83 mL |
| IPA | 200 µL |

B. Application of Solutions to Surfaces

Six-well plates (plasma-treated cyclic olefin copolymer (TOPAS®)) 96 well plates or polystyrene plates were removed from packaging and placed in large nitrogen purge box which is continuously being purged with nitrogen gas. The humidity level in the purge box was less than 30% before dispensing formulations. A semi-automated pipettor was set to 250 µL and 26 µL and dispensed into each well. The 6wp contained a lid with 6 "drilled holes" which allow for dispensing the formulation while at the same time controlling the evaporation rate. Once the desired amount was dispensed a solid template was placed over the drilled holes. The plate was carried to the vacuum oven and the formulation was allowed to spread for approximately 30 seconds. (Prior to this step that vacuum pump and refrigerant was turned on to ensure almost complete removal of ethanol and IPA). The solid lid was removed and replaced with a filter paper over the "drilled hole plate lid." Immediately the vacuum oven door was closed and the "vacuum" valve was adjusted to fully open. After the vacuum reached the maximum vacuum (25 to 30 in Hg.), there was a wait time of 5 minutes before closing the "vacuum" valve. The "purge" valve was released slowly until the gauge was down to "0." The instrument is designed to fill two microplates at a time. Plates were placed on trays in a hood for at least three hours until the ethanol evaporated.

C. UV Curing

A "Xenon Model RC-801 high intensity pulsed Ultraviolet (UV) light curing system", which employs the use of a single lamp that can simultaneously cure two 96 well plates at once was used in curing. The entire unit was enclosed in a chamber surrounded by a thick red curtain (UV radiation resistant). The chamber houses a purge box that holds both plates and ensures that the plates are constantly being purged with nitrogen which is necessary in order to create an inert environment (for the coatings) during curing. Once the plates have been placed in the nitrogen filled purge box and the UV chamber closed, the cure time is set (i.e. 60 sec. in this study). Also, a 60 sec purge time is also allowed prior to curing. Once the plates have been purged with nitrogen for at least 60 seconds, they are then cured. Nitrogen purging removes oxygen from chamber and prevents scavenging or inhibition. After curing, the plates were inspected to ensure that they were properly cured; the next set of plates was cured until the desired number of plates required for curing was achieved. The plates were then set aside for quality check using crystal violet staining.

D. Peptide Conjugation

Into a 20 ml centrifuge tube, 1 mM peptide solution at pH 7.4, 25 mM PBS buffer in the amount of 1.5 mL was added to each of the 6 wells. The 6 well plates were placed on the shaker at a speed of 6 rpm and the peptide was allowed to react for 1.0-1.5 h. After the reaction was complete, the peptide was removed from the wells using an aspirator. A blocking solution of 1 M ethanolamine with pH adjusted to 8.0 to 8.5 with 37% HCl was added to each well to be blocked in the amount of 1.5 mL. The 6 well plates were placed on the shaker for 1.0-1.5 h to allow quenching of NHS groups on the surface. Directly following the blocking step, the blocking solution was aspirated removing all of the blocking solution completely. Subsequently, each well was filled with 200 µL of 25 mM of phosphate buffer using a single pipettor. The buffer was then removed by aspiration after 2-5 minutes. This step was repeated 3 times, before adding DI water to the wells in the same manner, repeated 3 times. The wells were then filled with 100 µL of 1% SDS solution and the holes covered with a lid then placed on shaker between 15 minutes to overnight. The wells were refilled with 300 µL of DI and aspirated completely. The plates were dried in dry ambient conditions or in vacuum oven at room temperature. After drying, plates were generally individually thermo sealed in plastic pouches and stored at 2-4° C. The formulations shown in Tables 3 and 4 resulted in uniform cell culture surfaces, as shown by crystal violet and fluorescence measurements.

EXAMPLE 3

Cell Culture

A. Stock Culture of hESC Cell

H1 hES cells were cultured on Matrigel-coated TCT flasks in chemically defined culture medium (X-Vivo-10, 80 ng/ml hbFGF, 0.5 ng/ml hTGF-β1). Cells were passaged every 5-6 days at the seeding density of $5 \times 10^6$ cells/T-75. For the experiments, cells were seeded at a density of 33,000 cells/well on Matrigel-coated or (meth)acrylate-coated 96-well plates using MultidropCombi (ThermoFisher) automated dispenser and cultured for 48 hrs in the same culture medium supplemented with 20% fetal bovine serum (FBS).

B. Prior to cell seeding, synthetic polymer surfaces prepared in the 6-well format (wells and lids) were sprayed with 70% ethanol and left to evaporate in a sterile laminar flow hood overnight. All wells were then washed twice with Dulbecco's Phosphate Buffered Saline (DPBS) to remove any residual ethanol. H1 hESCs were cultured on synthetic polymer surfaces conjugated with Ac-KGGNGEPRGDTYRAY-NH$_2$ (BSP peptide) (SEQ ID NO:1) in chemically defined cell culture medium (X-Vivo-10, 80 ng/mL hbFGF, 0.5 ng/mL hTGF-β1). Cells were seeded at the density of $0.8 \times 10^6$/well and medium was exchanged daily after 48 hours. Cells were cultured for 48 hrs under standard cell culture conditions (37° C. with 5% $CO_2$). On day 5, cells were crystal violet stained for assessment of cell morphology. MATRIGEL™-coated wells were used as positive control for adhesion and growth of undifferentiated hES cells. Cells were cultured for 48 hrs under standard cell culture conditions (37° C. with 5% $CO_2$).

Figure 5:
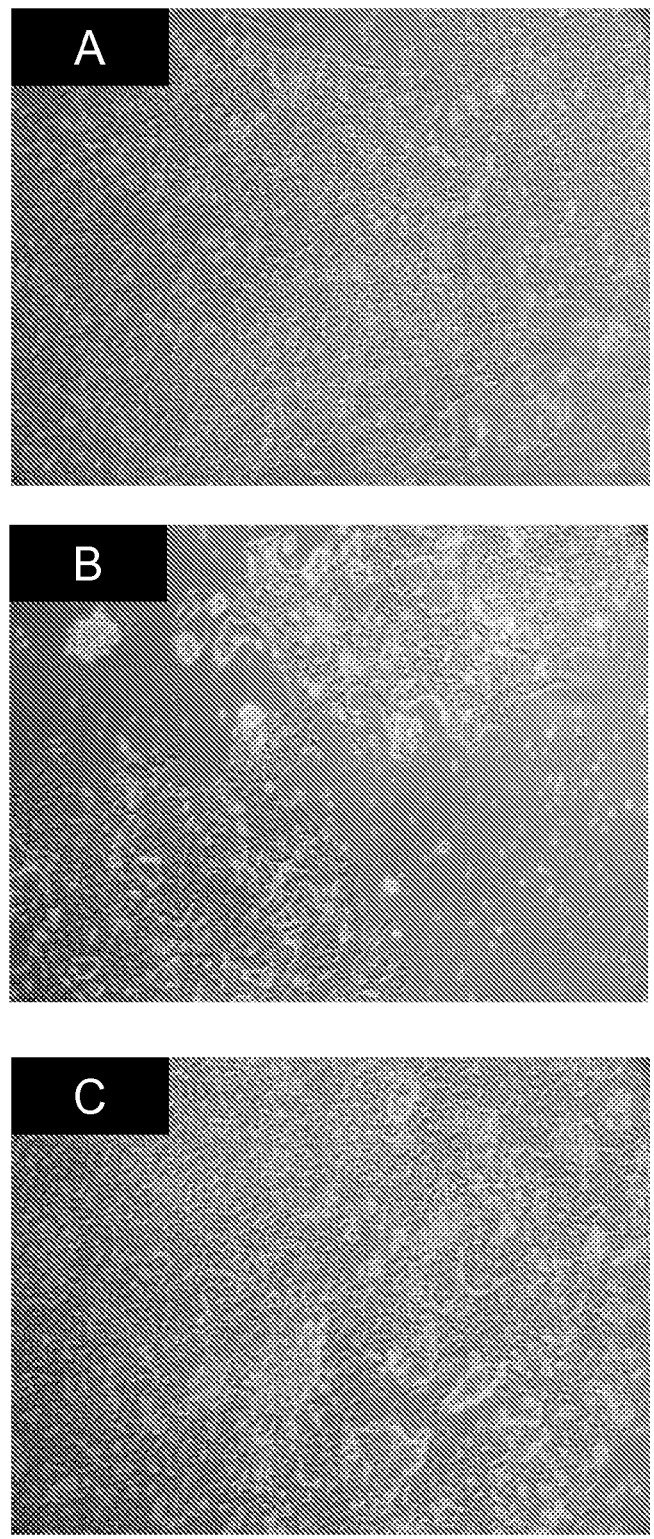
FIG. 5A-C are micrographs showing morphology of H1 human embryonic stem cells after culturing them on embodiments of peptide-conjugated synthetic polymer surfaces made from embodiments of monomers of the present invention.

Cells were washed with 150 µl DPBS and analyzed with light microscopy (see FIG. 5 H1 hES colony morphology on synthetic polymer surfaces compared to the colony morphology on Matrigel™ (positive control). FIG. 5A shows BCIP staining for cells grown on Matrigel™ (96 hours). FIG. 5B shows BCIP staining for H1 hEScells grown on the formulation shown in Table 3 conjugated to SEQIDNO:1 peptide. FIG. 5C shows BCIP staining for H1 hES cells grown on the formulation shown in Table 4 conjugated to the BSP peptide (SEQIDNO:1). Note the similar cell morphology and colony formation.

Both of the formulations shown in Tables 3 and 4 resulted in peptide conjugated synthetic polymer surfaces that may be suitable for cell culture, especially culture of undifferentiated H1 human embryonic stem cells, in the absence of serum. This peptide-conjugated synthetic polymer surface provided a surface that was comparable to that seen for the same cells on Matrigel™. As discussed above, these cells are particularly difficult to culture, requiring conditions that allow these cells to remain in culture without differentiating.

The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

We claim:

1. A synthetic polymeric cell culture surface comprising the polymer comprising a polymer comprising mono-(2-methacryloyloxyl)-ethyl succinate N-hydroxysuccinimide ester, hydrophilic monomer and a crosslinker.

2. A peptide-conjugated polymeric cell culture surface comprising a polymer made from mono-(2-methacryloyloxyl)-ethyl succinate N-hydroxysuccinimide ester, 2-hydroxyethyl methacrylate, and tetraethyleneglycol dimethacrylate wherein the polymer is conjugated to an RGD-containing peptide.

3. The peptide-conjugated polymeric cell culture surface of claim 2 wherein the RGD-containing peptide is KGGNGEPRGDTYRAY (SEQ ID NO:1).

4. A cell culture surface comprising the polymer of claim 1 comprising a polymer comprising 2-carboxyethylacrylate N-hydroxysuccinimide ester, hydrophilic monomer and a crosslinker.

5. A peptide-conjugated polymeric cell culture surface comprising a polymer made from 2-carboxyethyl acrylate N-hydroxysuccinimide ester, 2-hydroxyethyl methacrylate, and tetraethyleneglycol dimethacrylate wherein the polymer is conjugated to an RGD-containing peptide.

6. The peptide-conjugated polymeric cell culture surface of claim 5 wherein the RGD-containing peptide is KGGNGEPRGDTYRAY (SEQ ID NO:1).

* * * * *

SEQUENCE LISTING

<160> NUMBER OF SEQ ID NOS: 23

<210> SEQ ID NO 1
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 1

Lys Gly Gly Asn Gly Glu Pro Arg Gly Asp Thr Tyr Arg Ala Tyr
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 2

Asn Gly Glu Pro Arg Gly Asp Thr Tyr Arg Ala Tyr
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 3

Gly Arg Gly Asp Ser Pro Lys
1               5

<210> SEQ ID NO 4
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 4

Ala Val Thr Gly Arg Gly Asp Ser Pro Ala Ser Ser
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 5

Pro Gln Val Thr Arg Gly Asp Val Phe Thr Met Pro
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 6

Arg Asn Ile Ala Glu Ile Ile Lys Asp Ile

```
1               5                   10
```

<210> SEQ ID NO 7
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 7

```
Lys Tyr Gly Arg Lys Arg Leu Gln Val Gln Leu Ser Ile Arg Thr
1               5                   10                  15
```

<210> SEQ ID NO 8
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 8

```
Asn Gly Glu Pro Arg Gly Asp Thr Arg Ala Tyr
1               5                   10
```

<210> SEQ ID NO 9
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 9

```
Asn Gly Glu Pro Arg Gly Asp Thr Tyr Arg Ala Tyr
1               5                   10
```

<210> SEQ ID NO 10
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 10

```
Lys Tyr Gly Ala Ala Ser Ile Lys Val Ala Val Ser Ala Asp Arg
1               5                   10                  15
```

<210> SEQ ID NO 11
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 11

```
Lys Tyr Gly Lys Ala Phe Asp Ile Thr Tyr Val Arg Leu Lys Phe
1               5                   10                  15
```

<210> SEQ ID NO 12
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 12

```
Lys Tyr Gly Ser Glu Thr Thr Val Lys Tyr Ile Phe Arg Leu His Glu
1               5                   10                  15
```

<210> SEQ ID NO 13
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 13

Lys Tyr Gly Thr Asp Ile Arg Val Thr Leu Asn Arg Leu Asn Thr Phe
1               5                   10                  15

<210> SEQ ID NO 14
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 14

Thr Ser Ile Lys Ile Arg Gly Thr Tyr Ser Glu Arg
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 15

Thr Trp Tyr Lys Ile Ala Phe Gln Arg Asn Arg Lys
1               5                   10

<210> SEQ ID NO 16
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 16

Ser Ile Asn Asn Asn Arg Trp His Ser Ile Tyr Ile Thr Arg Phe Gly
1               5                   10                  15

Asn Met Gly Ser
            20

<210> SEQ ID NO 17
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 17

Lys Tyr Gly Leu Ala Leu Glu Arg Lys Asp His Ser Gly
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 18

Gly Gln Lys Cys Ile Val Gln Thr Thr Ser Trp Ser Gln Cys Ser Lys
1               5                   10                  15

Ser

<210> SEQ ID NO 19
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 19

Lys Gly Gly Lys Asp Gly Glu Pro Arg Gly Asp Thr Tyr Arg Ala Thr
1               5                   10                  15

Asp

<210> SEQ ID NO 20
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 20

Lys Gly Gly Leu Glu Pro Arg Gly Asp Thr Tyr Arg Asp
1               5                   10

<210> SEQ ID NO 21
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 21

Lys Gly Gly Cys Asn Gly Glu Pro Arg Gly Asp Thr Tyr Arg Ala Thr
1               5                   10                  15

Cys

<210> SEQ ID NO 22
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 22

Lys Gly Gly Cys Glu Pro Arg Gly Asp Thr Tyr Arg Cys
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 23

Lys Gly Gly Ala Val Thr Gly Asp Gly Asn Ser Pro Ala Ser Ser
1               5                   10                  15